United States Patent [19]

Patterson

[11] Patent Number: 5,447,950
[45] Date of Patent: Sep. 5, 1995

[54] ANTHRA[1,9-C,D]PYRAZOL-6-(2H)-ONES USEFUL FOR TREATING ANAEROBIC BACTERIAL INFECTIONS

[75] Inventor: Laurence H. Patterson, Leicester, England

[73] Assignee: British Technology Group Limited, London, England

[21] Appl. No.: 133,034

[22] Filed: Oct. 22, 1993

[30] Foreign Application Priority Data

Apr. 12, 1991 [GB] United Kingdom ............. 9107852

[51] Int. Cl.⁶ ................. A61K 31/415; C07D 231/54
[52] U.S. Cl. ................................. 514/406; 514/403; 548/356.5
[58] Field of Search ............ 514/403, 406, 925; 548/356.5

[56] References Cited

U.S. PATENT DOCUMENTS

| 3,174,994 | 3/1965 | Sutton | 560/101 |
|---|---|---|---|
| 4,686,218 | 8/1987 | Marinis et al. | 514/213 |
| 4,963,554 | 10/1990 | Combs et al. | 514/259 |

FOREIGN PATENT DOCUMENTS

| 0103381 | 3/1984 | European Pat. Off. |
|---|---|---|
| 0138302 | 4/1985 | European Pat. Off. |
| 0145226 | 6/1985 | European Pat. Off. |
| 254224A2 | 1/1988 | European Pat. Off. |
| 1118414 | 6/1956 | France |
| 1316453 | 12/1962 | France |
| 1942185 | 8/1968 | Germany |
| 3405330A1 | 8/1985 | Germany |
| WO91/05824 | 5/1991 | WIPO |
| 92-18469 | 10/1992 | WIPO |

OTHER PUBLICATIONS

A. Paul Krapcho et al. "Synthesis and antitumor evaluations of symmetrically and unsymmetrically substituted 1,4-Bis . . . " J. Med. Chem. 1991, 34, pp. 2373–2380.
J. Med. Chem., 1989, 24. Karzhendler et al. "Synthesis of aminoanthraquinone . . . ", pp. 23–30.
Stefenska, et al. "Synthesis of Unsymmetrically . . . " European J. Med. Chem., 1989 32, pp. 1724–1728.
Cheng et al. "The design synthesis . . . " Progress in Medicinal Chemistry, 1983, 20, pp. 83–118.
Fujiwara et al. "N-oxides and . . . " J. Het. Chem. 1969, 6, pp. 389–392.
Langendoen et al. "An approach to novel . . . " Tetrahedron, 1988, 44, pp. 3627–3631.

(List continued on next page.)

*Primary Examiner*—Jacqueline Haley
*Attorney, Agent, or Firm*—Nixon & Vanderhye

[57] ABSTRACT

Compounds of formula (I)

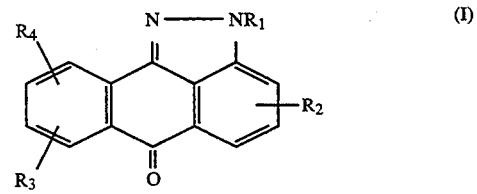

in which $R_1$ is A-N(O)R'R" and $R_2$, $R_3$ and $R_4$ are each separately selected from hydrogen, X and NH-A-N(O)R'R" wherein X is hydroxy, halogeno, amino, $C_{1-4}$ alkoxy or $C_{2-18}$ alkanoyloxy, A is a $C_{2-4}$ alkylene group with a chain length between N or NH and N(O)R'R" of at least 2 carbon atoms and R' and R" are each separately selected from $C_{1-4}$ alkyl groups and $C_{2-4}$ hydroxyalkyl and $C_{3-4}$ dihydroxyalkyl groups in which the carbon atom attached to the nitrogen atom does not carry a hydroxy group and no carbon atom is substituted by two hydroxy groups, or R' and R" together are a $C_{2-6}$ alkylene group which with the nitrogen atom to which R' and R" are attached forms a heterocyclic group having 3 to 7 atoms in the ring, and physiologically acceptable salts thereof are of value in the treatment of anaerobic bacterial infections.

12 Claims, No Drawings

OTHER PUBLICATIONS

Langendoen et al. "Regiospecific C-9 substitution . . ." Terahedron, 1989, 45, pp. 1759–1762.

Brunston et al. "Alcaloides Des . . ." Photochemistry, 1972, 11, pp. 3073–3075.

Bild et al. "Notiz uber die . . ." Helvetica Chimica Acta, 1967, 50, pp. 1885–1892.

Jarman et al. "Analogues of tamoxifen . . ." Anti-Cancer Drug Design, 1986, 1 pp. 259–268.

Zeman et al. "SR–4233: A new bioreductive agent" Int. J. Radiation Oncology, Biol. Phys., 1986, 12, pp. 1239–1242.

Jenkins. "Hypoxia–selective agents . . ." The Chemistry of Antitumor Agents, Wilman (eds.), 1990, pp. 342–369.

Hulbert et al. "Hycanthone analogs . . ." Science, 1974, 186 pp. 647–648.

Connars. "Alkylating prodrugs in . . ." Structure-Activity Relationship of Anti–tumor Agents, 1983, pp. 47–57.

Wilson et al. "Bis–Bioreductive agents . . ." 7th Intl Conf. on Chem. Modifiers of Cancer Treatment, Florida, USA, Feb. 2–5, 1991, p. 248.

Proceedings, 83rd Annual Meeting of the American Association for Cancer Research, May 20–23, 1992, San Diego, Calif., USA, vol. 33, Mar. 1992.

NCI–EORTC symposium on new drugs in cancer therapy. Amsterdam, Mar. 17–20, 1992.

ANTHRA[1,9-C,D]PYRAZOL-6-(2H)-ONES USEFUL FOR TREATING ANAEROBIC BACTERIAL INFECTIONS

This application is a National Stage Application of PCT/GB92/00645 filed Apr. 10, 1992, now WO 92/18485, published Oct. 29, 1992.

ANTI-CANCER COMPOUNDS

This invention relates to novel anthrapyrazoles which are of particular value in the treatment of cancer.

Aminoalkyl anthrapyrazoles have been described for use as chemotherapeutic agents for the treatment of cancer. However, in common with other cytotoxic chemotherapeutic agents these anthrapyrazoles have the disadvantage that their activity is not confined to neoplastic cells and they therefore exhibit various undesirable side effects.

It is an object of the present invention to provide a group of anthrapyrazole and pyrazoloacridine pro-drugs which are of lesser cytotoxicity than the drug itself, preferably being substantially non-cytotoxic, the pro-drugs being converted in vivo to the cytotoxic drug, especially under the anaerobic conditions within neoplastic tissue, thereby mitigating the side effects of administering that drug directly.

Accordingly the present invention comprises a compound of formula (I)

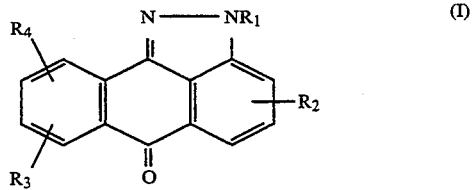

in which $R_1$ is A-N(O)R'R" and $R_2$, $R_3$ and $R_4$ are each separately selected from hydrogen, X and NH-A-N(O)R'R" wherein X is hydroxy, halogeno, amino, $C_{1-4}$ alkoxy or $C_{2-8}$ alkanoyloxy, A is a $C_{2-4}$ alkylene group with a chain length between N or NH and N(O)R'R" of at least 2 carbon atoms and R' and R" are each separately selected from $C_{1-4}$ alkyl groups and $C_{1-4}$ hydroxyalkyl and $C_{3-4}$ dihydroxyalkyl groups in which the carbon atom attached to the nitrogen atom does not carry a hydroxy group and no carbon atom is substituted by two hydroxy groups, or R' and R" together are a $C_{2-6}$ alkylene group which with the nitrogen atom to which R' and R" are attached forms a heterocyclic group having 3 to 7 atoms in the ring, the compound optionally being in the form of a physiologically acceptable salt.

The compounds of formula (I) contain at least one tertiary nitrogen atom in N-oxide form. Anti-cancer drugs containing a group of this type are not unknown. However, although anthrapyrazole drugs are known for various uses, we are not aware of any previous disclosure of anthrapyrazole anti-cancer drugs which contain a tertiary nitrogen atom in N-oxide form. Moreover, the N-oxide compounds of the present invention have the particular value that they are pro-drugs of lower cytotoxicity which generate a toxic drug in vivo. Thus it is believed that the N-oxides of the present invention are bioreductively activated within neoplastic tissue to form the cytotoxic compound containing the tertiary nitrogen atom without the oxide atom, thereby providing the desired anti-cancer activity of this compound but with mitigation of its undesired side effects.

A similar approach to that of the present invention is described for aminoalkylamino anthraquinones in UK Patent Application No. GB 2237283 and PCT Application No. GB 90/01574.

As regards the groups A-N(O)R'R" and NH-A-N(O)R'R", A (which may differ among two or more such groups present in the compound) may be branched but is conveniently a straight chain alkylene group, i.e. tetramethylene, especially trimethylene or ethylene.

R' and R" (which again may differ among two or more such groups present in the compound) may also have a branched carbon chain but are conveniently straight chain whether they are alkyl groups or hydroxy-substituted alkyl groups. When R' or R" is a monohydroxyalkyl group this is conveniently substituted terminally and when R' or R" is a dihydroxyalkyl group this will be substituted terminally by one of the hydroxy groups for a $C_3$ group and conveniently is also so substituted for a $C_4$ group. When R' and R" are alkyl the preference is for a group of three or especially two or one carbon atoms and when R' and R" are hydroxy-substituted alkyl the preference is for the alkyl group to be of three carbon atoms or, in the case of a monohydroxyalkyl group, alternatively of two carbon atoms. Examples of preferred individual groups R' and R" are $CH_2CH_2CH_3$, $CH_2CH_2OH$, $CH_2CH_2CH_2OH$, $CH(CH_3)CH_2OH$ and $CH_2CHOHCH_2OH$ and especially $CH_3$ and $CH_2CH_3$. Whilst R' and R" will more usually be identical there can be certain advantages as indicated hereinafter in having non-identical groups R' and R".

Alternatively R' and R" together with the nitrogen atom to which they are attached may represent a heterocyclic group —N(CH$_2$), where n is 2 to 6, i.e. aziridin-1-yl, azetidin-1-yl, pyrrolidin-1-yl, piperidin-1-yl and perhydroazepin-1-yl, the smaller groups such as azetidin-1-yl and especially aziridin-1-yl being of most interest.

Specific groups A-N(O)R'R" of particular interest are $(CH_2)_2$-N(O)(CH$_3$)C$_2$H$_5$, $(CH_2)_2$-N(O)(CH$_2$CH$_2$OH)$_2$, $(CH_2)_2$-N(O)(CH$_2$CH$_2$CH$_2$OH)$_2$, $(CH_2)_2$-N(O)(CH(CH$_3$)CH$_2$OH)$_2$, $(CH_2)_2$-N(O)(CH$_2$CHOHCH$_2$OH)$_2$, especially $(CH_2)_2$-N(O)(CH$_3$)$_2$ and $(CH_2)_2$-N(O)(C$_2$H$_5$)$_2$, and also the corresponding groups in which —(CH$_2$)$_2$— is replaced by —(CH$_2$)$_3$—.

Specific groups NH-A-N(O)R'R" of particular interest are NH-(CH$_2$)$_2$-N(O)(CH$_3$)C$_2$H$_5$, NH-(CH$_2$)$_2$-N(O)(CH$_2$CH$_2$OH)$_2$, NH-(CH$_2$)$_2$-N(O)(CH$_2$CH$_2$CH$_2$OH)$_2$, NH-(CH$_2$)$_2$-N(O)(CH(CH$_3$)CH$_2$OH)$_2$, NH-(CH$_2$)$_2$-N(O)(CH$_2$CHOHCH$_2$OH)$_2$, especially NH-(CH$_2$)$_2$-N(O)(CH$_3$)$_2$ and NH-(CH$_2$)$_2$-N(O)(C$_2$H$_5$)$_2$, and also the corresponding groups in which —(CH$_2$)$_2$— is replaced by —(CH$_2$)$_3$—.

Halogeno as used herein includes fluoro, chloro, bromo and iodo but, as regards the groups X, the halogeno groups are preferably bromo and especially chloro. Alkoxy and alkanoyloxy groups X may be branched or especially straight chain and are conveniently of 1 or 2 carbon atoms for the alkoxy groups and of 2 or 3 carbon atoms for the alkanoyloxy groups. Specific examples of groups X are chloro, amino, methoxy, ethoxy, acetyloxy and propionyloxy. However hydroxy groups are preferred as the group or groups X.

Formula (II) illustrates the system used for numbering the various positions of the anthrapyrazole systems.

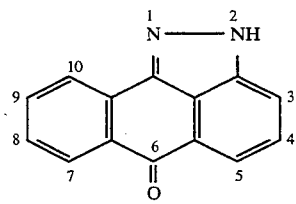

It will be seen from this formula that the ring system is fully asymmetrical so that none of the positions are equivalent. Preferences as to positions of substitution are expressed herein by identifying groups $R_3$ and $R_4$ which are other than hydrogen in that order, i.e. where there is one substituent at positions 7 to 10 that substituent is identified as $R_3$ with $R_4$ being hydrogen.

In addition to the group $R_1$ of the form A-N(O)R'R'' at position 2 up to three of any of positions 3, 4, 5, 7, 8, 9 and 10 in the compound (I) may in addition be substituted by a group NH-A-N(O)R'R'' but positions 5 and 7 are of most interest for substitution by such a group and, indeed, together with position 10, also by the other substituent groups. Where more than one acyclic group containing a tertiary nitrogen atom in N-oxide form [A-N(O)R'R'' in the case of $R_1$ and NH-A-N(O)R'R'' in the case of $R_2$, $R_3$ and $R_4$] is present these may be different as regards A and/or R' and R'' but are conveniently identical. Although three or four of such groups may be present, preferred compounds contain either one such group, this being $R_1$, or two such groups, conveniently with a 2,7 or especially a 2,5 substitution pattern for these groups (so that $R_1$ is a group A-N(O)R'R'' at the 2-position together with either $R_2$ being a group NH-A-N(O)R'R'' at the 5-position or $R_3$ being a group NH-A-N(O)R'R'' at the 7-position).

The compounds (I) may optionally contain one, two or three groups X depending on the number of groups NH-A-N(O)R'R'' which are present. Thus, for example, up to three groups X may be present when no groups NH-A-N(O)R'R'' are present and up to two groups X may be present when only one group NH-A-N(O)R'R'' is present, such groups X being the same or different. A group X may be at any of positions 3, 4, 5, 7, 8, 9 and 10 but such a group may conveniently be at one or more of the positions 10, especially 5 and particularly 7, providing these are not occupied by a group NH-A-N(O)R'R''. Compounds substituted by groups X, especially hydroxy groups, are of particular interest. Conveniently one or both of positions 7 and 10 may be occupied by a group X, particularly a hydroxy group in each case. In a preferred group of compounds $R_2$ is either hydrogen or more particularly a group NH-A-N(O)R'R'' at position 5 and position 7, position 10 or both positions 7 and 10 are occupied by a group X, particularly a hydroxy group in each case, with a position 7 or 10 which is unoccupied by a group X optionally being occupied by a group NH-A-N(O)R'R''. Thus, in general, compounds having a group X at least at one of positions 7 and 10, particularly a hydroxy group in each case, are of some interest, for example those indicated under (1), (3), (5) and (7) below.

Compounds of particular interest thus have one of:

(1) $R_1$=A-N(O)R'R'', $R_2$=OH (position 5), $R_3$=$R_4$=H;

(2) $R_1$=A-N(O)R'R'', $R_2$=H, $R_3$=OH (position 7 or 10), $R_4$=H;

(3) $R_1$=A-N(O)R'R'', $R_2$=H, $R_3$=$R_4$=OH (positions 7 and 10);

(4) $R_1$=A-N(O)R'R'' and $R_2$=NH-A-N(O)R'R'' (position 5) with A, R' and R'' in $R_1$ and $R_2$ conveniently being identical groups, $R_3$=OH (positions 7 or 10), $R_4$=H; and (5) $R_1$=A-N(O)R'R'' and $R_2$=NH-A-N(O)R'R'' (position 5) with A, R' and R'' in $R_1$ and $R_2$ conveniently being identical groups, $R_3$=$R_4$=OH (positions 7 and 10).

Of these, the compounds of types (4) and (5) are preferred.

Also of interest are compounds in which the only substituents are groups selected from A-N(O)R'R'' and NH-A-N(O)R'R'', for example the compounds of types (1) and (4) in which any group indicated as OH is instead H, the compounds derived from those of type (4) being preferred.

Specific compounds (I) according to the present invention include those compounds of types (1) to (5) just listed, and the variants thereof, in which the or each group of A-N(O)R'R'' and NH-A-N(O)R'R'' has A=$(CH_2)_3$ or particularly $(CH_2)_2$ and R' and R'' are each separately $CH_2CH_2CH_3$, $CH_2CH_2OH$, $CH_2CH_2CH_2OH$, $CH(CH_3)CH_2OH$ or $CH_2CHOHCH_2OH$, especially $CH_2CH_3$ or particularly $CH_3$. Preferably R' and R'' are identical for each group A-N(O)R'R'' and NH-A-N(O)R'R'' and preferably where two such groups are present the groups A are identical, the various groups R' and R'' conveniently also being identical. However it is readily possible to produce compounds having the group A-N(O)R'R'' and one group NH-A-N(O)R'R'' in which R' and R'' are identical within each group but differ from one group to the other, and also where A differs if desired.

Particularly preferred specific compounds are those of formula (III) and particularly of formula (IV), in which Y and Y' are separately each H or OH, and their analogues in which the two methyl groups in N(O)(CH$_3$)$_2$ are replaced by two n-propyl, 2-hydroxyethyl, 2-hydroxypropyl, 3-hydroxypropyl, 2,3-dihydroxypropyl or particularly ethyl groups, including, in the case of (IV), compounds in which the terminal dialkyl groups vary between the two substituents. All of these compounds may be in the free base or a salt form. In the most preferred compounds at least one of Y and Y' is OH, i.e. Y=OH, Y'=H, Y=H, Y'=OH or Y=Y'=OH, in each of (III) and (IV).

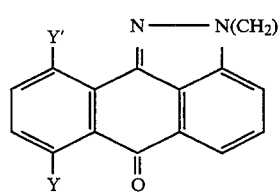

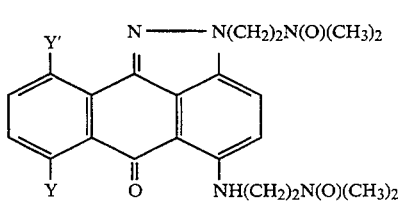

Certain substituents in the compounds (I) may contain one or more asymmetric carbon atoms and the compounds will then exist in stereoisomeric forms. Moreover, in the case where R' and R" are different this will introduce a centre of asymmetry at the nitrogen atom in N-oxide form. It will be appreciated that one stereoisomeric form of a compound may be of particular interest by virtue of advantageous physical properties, for example greater solubility, or biological activity, for example by virtue of greater ease of enzymic reduction.

As indicated the compounds (I) may be used in the form of a physiologically acceptable salt which will generally be an acid addition salt with an organic or inorganic acid. Examples of such inorganic acids are hydrochloric, hydrobromic, hydroiodic, phosphoric and sulphuric. Examples of such organic acids are acetic, ascorbic, benzoic, citric, fumaric, gluconic, isethionic, lactic, maleic, malic, methane sulphonic, oxalic, succinic, sulphamic and tartaric. Of these the hydrohalic acids and especially hydrochloric acid are of particular interest. Although the salts will usually have similar physiological properties to the free base they may have the advantage of enhanced solubility, etc.

The compounds (I) may conveniently be prepared through the oxidation of the tertiary amino group(s) of the corresponding compound in which each group A-N(O)R'R" and NH-A-N(O)R'R" in the compound (I) is in the form A-NR'R" and NH-A-NR'R", respectively. Thus, for example, anthrapyrazoles containing various [2-(dialkylamino)ethyl]amino, {2-[di-(hydroxyalkyl)amino]ethyl}amino and [2-(cyclic alkyleneamino)ethyl]amino groups may be oxidized to the ω-N-oxides. Where appropriate the precursor compound which is oxidized may contain one or more modified groups X, R' and R" as compared with the parent compound, the groups X, R' and R" corresponding to those in the compound (I) being generated after the oxidation has been effected. In general, however, it is desirable that the precursor corresponds to the final compound apart from the presence of N instead of N(O).

Any suitable oxidizing agent for converting a tertiary aliphatic amine to N-oxide form may be used, for example aqueous hydrogen peroxide/methanol (Foster et al, Biochem. Pharmacol., 1980, 29, 1977), oxone (potassium peroxymonosulphate) (Kennedy et al, Journal of Organic Chemistry, 1960, 1901), tetra-n-butylammonium octamolybdate (Jarman et al, Anti-Cancer Drug Design, 1986, 1, 259), and a peracid such as m-chloroperbenzoic acid (Craig et al, Journal of Organic Chemistry, 1970, 35, 1721). The last mentioned reagent is preferred, reaction at room temperature or at a lower temperature of down to −70° C. in the dark overnight with an excess of such an acid is usually sufficient to effect conversion to the N-oxide.

Where the compound (I) can exist in d and l forms as well as the dl form an optically active isomer may be synthesised either substantially free from these other forms, or at least in a major proportion by weight as compared with them, either by using optically active reagents in the synthesis of the compound or, particularly in the case of the optically active compounds in which R' and R" are different, by resolving the dl form, especially by using an optically active inorganic or organic acid to provide two stereoisomeric salts with different physical properties. In such an instance and also where the compound (I) is used in the form of a salt the salt may be prepared by reaction of the organic base (I) with the appropriate inorganic or organic acid according to conventional procedures, usually by simple admixture in solution. The acid addition salts are generally crystalline solids which are relatively soluble in water, methanol, ethanol and similar solvents.

Accordingly the present invention comprises a process for the preparation of a compound of formula (I) as defined hereinbefore which comprises oxidizing a compound of formula (Ia)

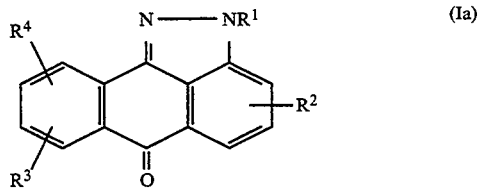

in which R$^1$ is A-NR'R" wherein A, R' and R" correspond to the groups in R$_1$, R$^2$, R$^3$ and R$^4$ correspond to R$_2$, R$_3$ and R$_4$, respectively, in the compound (I) but with each of the groups of the type NH-A-N(O)R'R" in the compound (I) being instead a group NH-A-NR'R" in the compound (Ia), one or more groups X, R' and R" in the compound (Ia) optionally instead being modified to a form convertible to said group or groups present in the compound (I), and where appropriate converting the one or more so modified groups X, R' and R" in the compound (Ia) to the form present in the compound (I) and/or forming an acid addition salt with a physiologically acceptable organic or inorganic acid.

Various routes are available for the synthesis of the intermediates which are oxidized to the compounds (I) of the present invention as will be apparent to the man skilled in the art from the literature, for example, procedures such as those described in various of the literature references of Chapters 1 and 2, in particular, of The Chemistry of Antitumour Agents, 1990, Wilman (editor), published by Blackie (London) and Chapman and Hall (New York) or modifications of those procedures. Examples of particular literature references are Showalter et al, Journal of Medicinal Chemistry, 1984, 27, 255-256 and 1987, 30, 121-131, and Sebolt et al, Cancer Research, 1987, 47, 4299.

Where one or more substituents X is present it may be appropriate, depending on the route of synthesis, to have these present throughout in their final form or to generate the desired groups at a later stage in the synthesis. Ether and ester groups X may of course readily be prepared by modification of hydroxy groups according to known procedures, precursors containing a hydroxy group X more often being described in the literature than those containing a corresponding ether or ester substituent. It may also be appropriate to synthesise compounds (I) containing an amino group via an intermediate containing a nitro group.

Certain of the intermediates corresponding to compounds (I) described herein but without the tertiary amine group(s) in N-oxide form are novel and are within the scope of this invention.

The compounds (I) may be formulated with a physiologically acceptable diluent or carrier for use as pharmaceuticals for both veterinary, for example in mammals, and particularly human use by a variety of methods. For instance, they may be applied as a composition incorporating a liquid diluent or carrier, for example an aqueous or oily solution, suspension or emulsion, which may often be employed in injectable form for parenteral administration and therefore may conveniently be sterile and pyrogen free. Oral administration may also be used and although compositions for this purpose may incorporate a liquid diluent or carrier, it is more usual to use a solid, for example a conventional solid carrier material such as starch, lactose, dextrin or magnesium stearate. Such solid compositions may take the form of powders but are more conveniently of a formed type, for example as tablets, cachets, or capsules (including spansules). Alternative, more specialized types of formulation include liposomes and nanoparticles.

Other types of administration than by injection or through the oral route which are of use in both human and veterinary contexts include the use of suppositories or pessaries. Another form of pharmaceutical composition is one for buccal or nasal administration. Other formulations for topical administration include lotions, ointments, creams, gels and sprays.

However, in the treatment of cancer parenteral and sometimes topical administration is often of particular interest.

Compositions may be formulated in unit dosage form, i.e. in the form of discrete portions containing a unit dose, or a multiple or sub-unit of a unit dose.

Whilst the dosage of the compound used will vary according to the activity of the particular compound and the condition being treated, it may be stated by way of guidance that a dosage selected in the range from 0.1 to 20 mg/kg of body weight per day, particularly in the range from 0.1 to 5 mg/kg of body weight per day, will often be suitable. However higher doses than this may be considered in view of the lower level of toxic side effects obtained with the compounds (I), for example in the range from 0.1 to 50 mg/kg of body weight per day or possibly even as high as described in U.S. Pat. No. 4,197,249 for the anthraquinone cancer drugs described therein, i.e. up to 200 mg/kg of body weight per day. This dosage regime may be continued for however many days is appropriate to the patient in question, the daily dosages being divided into several separate administrations if desired.

The compounds (I) are of particular value for the treatment of cancer in warm blooded animals including humans. The compounds are of interest in relation to the treatment of disseminated tumours such as leukaemias and lymphomas but more particularly of solid tumours such as various forms of sarcoma and carcinoma. Further information on dosage regimes and types of cancer to be treated may be obtained from the data on the corresponding or related compounds not containing the N-oxide group which is given in standard publications such as the ABPi Data Sheet Compendium published annually in the U.K. by Datapharm Publications Ltd., London, and in the Physicians' Desk Reference published annually in the U.S.A. by the Medical Economics Company, Inc., Oradell.

It may be advantageous to use the compounds (1) in a combined treatment, given separately or together in the same composition, with other anti-cancer agents, such as mitotic inhibitors, for example vinblastine; alkylating agents, for example cis-platin, carboplatin and cyclophosphamide; other antimetabolites, for example 5-fluorouracil, cytosine arabinoside and hydroxyurea; intercalating antibiotics, for example adriamycin and bleomycin; enzymes, for example asparaginase; topoisomerase inhibitors, for example etoposide and biological response modifiers, for example interferon.

In a variation of the usual procedure which relies upon the anaerobic conditions within neoplastic tissue to effect selective reduction of the N-oxide in such tissue, the selectivity as between neoplastic and normal tissue can be enhanced. Thus antibodies can be raised against tumours by conventional procedures, particularly using hybridoma technology, and linked covalently to a reductase using one of various conventional linking agents. The conjugate is administered to the patient when it localises in the body at the tumour site and the compound (I) is then administered, the action of the reductase enhancing the specificity of the action of the compound at the tumour site.

It should be appreciated that even where selective oxidation in hypoxic tissue is not playing a major role in the in vivo action of the compounds, they may still exert a valuable anti-cancer effect, for example where the compounds are reduced in the liver.

The compounds of formula (I) are also of potential value in the treatment of anaerobic bacterial infections. Representative of infectious diseases that may be treated with the compounds and compositions of the present invention include, for example, post-operative sepsis following lower gastrointestinal surgery or female urogenital surgery, pelvic inflammatory disease, ulcers, gangrene, trichomonal vaginitis, non-specific vaginitis, amoebiasis, giardiasis, periodontal disease, acne and the like. The compounds may, for anti-bacterial use, be administered in the form of similar pharmaceutical compositions which are used for the anti-cancer use and at similar dosage levels.

The present invention thus includes a method suitable for aiding regression and palliation of cancer or for the treatment of an anaerobic bacterial infection which comprises administering to a patient a therapeutically effective amount of a compound (I) as defined hereinbefore.

In addition to their anti-cancer use the compounds (I) are of interest for various other pharmaceutical applications in view of their activity as chelating agents.

The invention is illustrated by the following Examples.

EXAMPLE 1

Preparation of
2-[2-(dimethylamino-N-oxide)-ethyl]-5-{[2-(dimethylamino-N-oxide)ethyl]amino}anthra[1,9-cd]pyrazol-6(2H)-one (1)

2-[2-(Dimethylamino)-ethyl]-5-[2-(dimethylaminoethyl)amino]-anthra[1,9-cd]pyrazol-6(2H-one 0.4 g (0.001 mol) of 2-[2-(dimethylaminoethyl)amino]anthra[1,9-cd]-pyrazol-6(2H)-one is dissolved in 25 g dimethylaminoethylamine (0.28 mol) and the mixture is heated at reflux temperature under argon for 4 hours. The reaction mixture is then added to water, the precipitate collected by filtration and the filtrate evaporated to dryness in vacuo. The resulting residue is dissolved in a minimum volume of dichloromethane:methanol (90:10 v/v) and then chromatographed on a column of silica gel (60A) using an eluting solvent firstly of dichloromethane:methanol (90:10 v/v) and then of dichloromethane:methanol:triethylamine (90:9:1 v/v/v). The major yellow band is collected and evaporated in vacuo to yield 0.3 g of the title compound as a yellow solid, m.p. 112°–113° C.; $\lambda_{max}$ (distilled water)

(E/cm/M) 232 nm (19750), 464 nm (9605), 484 nm (9740).

(2)

2-[2-(Dimethylamino-N-oxide)-ethyl]-5-{[2-(dimethylamino-N-oxide)ethyl]amino}anthra[1,9-cd]pyrazol-6(2H)-one 0.2 g (0.00054 mol) of 2-[2-(dimethylamino)ethyl]-5-[2-(dimethylaminoethyl)amino]anthra-[1,9-cd]pyrazol-6(2H)-one is dissolved in 5 ml dichloromethane and the mixture cooled in an ice-bath whilst stirring. To this solution is added 0.32 g (0.00015 mol) of 3-chloroperbenzoic acid (80%) and the mixture left for 16 hours at 0° C. protected from light. Methanol (2 ml) is added and this solution is subject to flash column chromatography using a column of silica gel (60A) and an eluting solvent of dichloromethane:methanol:28% aqueous ammonia (49.5:49.5:0.5 v/v/v) followed by methanol:28% aqueous ammonia (90:10 v/v). The last eluting fraction is collected, filtered and evaporated in vacuo to yield 0.12 g of the title compound as a yellow solid, m.p. 120°–121° C.; $\lambda_{max}$ (distilled water) (E/cm/M) 230 nm (19830), 458 nm (8680), 482 nm (9170).

EXAMPLE 2

Preparation of
7,10-dihydroxy-2-[2-(dimethylamino-N-oxide)-ethyl]-5-[[2-(dimethylamino-N-oxide)ethyl]amino]anthra[1,9-cd]pyrazol-6(2H)-one (1)

7,10-Dihydroxy-2-[2-(dimethylamino)-ethyl]-5-[[2-(dimethylamino)ethyl]amino]anthra-[1,9-cd]pyrazol-6(2H)-one 0.35 g (0.59 mmol) of 2-[2-(dimethylamino)-ethyl]-5-[[2-(dimethylamino)ethyl]amino]-7,10-bis(phenylmethoxy)-anthra[1,9-cd]pyrazol-6(2H)-one is dissolved in cold, dry dichloromethane (4 ml) and boron trichloride (4 ml, 1M solution in dichloromethane) is added dropwise over 30 minutes under argon. The reaction mixture is maintained at 0°–5° C. for 1 hour and then treated dropwise with cold methanol under argon. The mixture is then maintained at room temperature for 2 hours and then evaporated to dryness in vacuo. The resulting crude hydrochloride salt is dissolved in a minimum volume of methanol and then chromatographed on a column of silica gel (60A) using an eluting solvent of dichloromethane:methanol (80:20 v/v) and then dichloromethane:methanol:triethylamine (80:20:1 v/v). The major red band is collected and evaporated in vacuo to yield 0.115 g of the title compound as a red solid, m.p. 101 C; $\lambda_{max}$ (methanol) (E/cm/M) 580 nm (11200), 334 nm (7463), 290 nm (5667).

(2)

7,10-dihydroxy-2-[2-(dimethylamino-N-oxide)-ethyl]-5-[[2-(dimethylamino-N-oxide)ethyl]amino]anthra[1,9-cd]pyrazol-6(2H)-one 0.130 g (0.32 mmol) of 7,10-dihydroxy-2-[2-(dimethylamino)-ethyl]-5-[[2-(dimethylamino)ethyl]amino]anthra-[1,9-cd]pyrazol-6(2H)-one is dissolved in 15 ml dry, cold dichloromethane and the mixture cooled to −20° C. whilst stirring. To this solution is added 0.151 g (0.70 mmol) of 3-chloroperbenzoic acid (80%), and left for 24 hours at −20° C. protected from light. Methanol (5 ml) is added and this solution is subject to flash column chromatography using a column of silica gel (60A) and an eluting solvent of dichloromethane: methanol: 880 ammonia (90:10:1 v/v/v) followed by methanol: 880 ammonia (99:1 v/v) and finally methanol: 880 ammonia (95:5 v/v). The last eluting fraction is collected, filtered and evaporated in vacuo to yield 0.115 g of the title compound a red solid, m.p. 132° C.; $\lambda_{max}$ (methanol) (E/cm/M) 514 nm (11273), 332 nm (5063).

EXAMPLE 3

Preparation of
7,10-dihydroxy-2-[2-(diethylamino-N-oxide)-ethyl]-5-[[2-(diethylamino-N-oxide)ethyl]amino]anthra[1,9-cd]pyrazol-6(2H)-one (1)

7,10-Dihydroxy-2-[2-(diethylamino)-ethyl]-5-[[2-(diethylamino)-ethyl]amino]anthra-[1,9-cd]pyrazol-6(2H)-one 0.100 g (0.148 mmol) 2-[2-(diethylamino)-ethyl]-5-[[2-(diethylamino)ethyl]amino]-7,10-bis(phenylmethoxy)-anthra[1,9-cd]pyrazol- 6(2H)-one is dissolved in cold, dry dichloromethane (4 ml) and boron trichloride (4 ml, 1M solution in dichloromethane) is added dropwise over 30 minutes under argon. The reaction mixture is maintained at 0°–5° C. for 1 hour and then treated dropwise with cold methanol under argon. The mixture is then maintained at room temperature for 2 hours and then evaporated to dryness in vacuo. The resulting crude hydrochloride salt is dissolved in a minimum volume of methanol and then chromatographed on a column of silica gel (60A) using an eluting solvent of dichloromethane:methanol (80:20 v/v) and then dichloromethane:methanol:triethylamine (80:20:1 v/v). The major red band is collected and evaporated in vacuo to yield 0.060 g of the title compound as an orange-red solid, m.p. 152° C.; $\lambda_{max}$ (methanol) (E/cm/M) 520 nm (22000).

(2)

7,10-Dihydroxy-2-[2-(diethylamino-N-oxide)-ethyl]-5-[[2-(diethylamino-N-oxide)ethyl]amino]anthra[1,9-cd]pyrazol-6(2H) -one 0.42 g (0.085 mmol) of 7,10-dihydroxy-2-[2-(diethylamino)-ethyl]-5-[[2-(diethylamino)ethyl]amino]anthra-[1,9-cd]pyrazol-6(2H)-one is dissolved in 15 ml dry, cold dichloromethane and the mixture cooled to −20° C. whilst stirring. To this solution is added 0.254 g (1.4 mmol) of 3-chloroperbenzoic acid (80%), and left for 24 hours at −20° C. protected from light. Methanol (5 ml) is added and this solution is subject to flash column chromatography using a column of silica gel (60A) and an eluting solvent of dichloromethane: methanol: 880 ammonia (90: 10:1 v/v/v) followed by methanol: 880 ammonia (99:1 v/v) and finally methanol: 880 ammonia (95:5 v/v). The last eluting fraction is collected, filtered and evaporated in vacuo to yield 0.020 g of the title compound as a dark red solid, m.p. 101° C. (decomp.) $\lambda_{max}$(methanol) (E/cm/M) 516 nm (15652).

I claim:

1. A compound of formula (I)

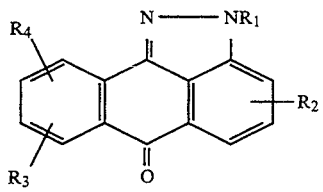

in which $R_1$ is $A\text{-}N(O)R'R''$ and $R_2$, $R_3$ and $R_4$ are each separately selected from hydrogen, X and NH-A-N(O)R'R'' wherein X is hydroxy, halogeno, amino, $C_{1-4}$ alkoxy or $C_{2-8}$ alkanoyloxy, A is a $C_{2-4}$ alkylene group with a chain length between N or NH and N(O)R'R'' of at least 2 carbon atoms and R' and R'' are each separately selected from $C_{1-4}$ alkyl groups and $C_{2-4}$ hydroxyalkyl and $C_{3-4}$ dihydroxyalkyl groups in which the carbon atom attached to the nitrogen atom does not carry a hydroxy group and no carbon atom is substituted by two hydroxy groups, or R' and R'' together are a $C_{2-6}$ alkylene group which with the nitrogen atom to which R' and R'' are attached forms a heterocyclic group having 3 to 7 atoms in the ring, the compound optionally being in the form of a physiologically acceptable salt.

2. A compound according to claim 1, in which $R_2$, $R_3$ and $R_4$ are each separately selected from hydrogen, hydroxy and NH-A-N(O)R'R''.

3. A compound according to claim 1, in which A is ethylene or trimethylene.

4. A compound according to claim 1, in which R' and R'' are each separately selected from $CH_3$, $CH_2CH_3$, $CH_2CH_2CH_3$, $CH_2CH_2OH$, $CH_2CH_2CH_2OH$, $CH(CH_3)CH_2OH$ and $CH_2CHOHCH_2OH$.

5. A compound according to claim 1, in which the group $A\text{-}N(O)R'R''$ is selected from $(CH_2)_n\text{-}N(O)(CH_3)_2$, $(CH_2)_n\text{-}N(O)(CH_3)(C_2H_5)$, $(CH_2)_n\text{-}N(O)(C_2H_5)_2$, $(CH_2)_n\text{-}N(O)(CH_2CH_2OH)_2$, $(CH_2)_n\text{-}N(O)(CH_2CH_2CH_2OH)_2$, $(CH_2)_n\text{-}N(O)(CH(CH_3)CH_2OH)_2$ and $(CH_2)_n\text{-}N(O)(CH_2CHOHCH_2OH)_2$, wherein n is 2 or 3.

6.- A compound according to claim 1 in which one of $R_2$, $R_3$ and $R_4$ is a group NH-A-N(O)R'R'' selected from $NH\text{-}(CH_2)_n\text{-}N(O)(CH_3)_2$, $NH\text{-}(CH_2)_n\text{-}N(O)(CH_3)C_2H_5$, $NH\text{-}(CH_2)_n\text{-}N(O)(C_2H_5)_2$, $NH\text{-}(CH_2)_n\text{-}N(O)(CH_2CH_2OH)_2$, $NH\text{-}(CH_2)_n\text{-}N(O)(CH_2CH_2CH_2OH)_2$, $NH\text{-}(CH_2)_n\text{-}N(O)(CH(CH_3)CH_2OH)_2$ and $NH\text{-}(CH_2)_n\text{-}N(O)(CH_2CHOHCH_2OH)_2$, wherein n is 2 or 3, and the other two of $R_2$, $R_3$ and $R_4$ are each separately hydrogen or a group X.

7. A compound according to claim 1, in which
(1) $R_1 = A\text{-}N(O)R'R''$ and $R_2 = R_3 = R_4 = H$; or
(2) $R_1 = A\text{-}N(O)R'R''$, $R_2 = NH\text{-}A\text{-}N(O)R'R''$ at position 5 and $R_3 = R_4 = H$.

8. A compound according to claim 1, in which
(1) $R_1 = A\text{-}N(O)R'R''$, $R_2 = OH$ at position 5, $R_3 = R_4 = H$;

(2) $R_1 = A\text{-}N(O)R'R''$, $R_2 = H$, $R_3 = OH$ at position 7 or position 10 and $R_4 = H$;
(3) $R_1 = A\text{-}N(O)R'R''$, $R_2 = H$ and $R_3 = R_4 = OH$ at positions 7 and 10;
(4) $R_1 = A\text{-}N(O)R'R''$, $R_2 = NH\text{-}A\text{-}N(O)R'R''$ at position 5 and $R_3 = OH$ at position 7 or 10 and $R_4 = H$; or
(5) $R_1 = A\text{-}N(O)R'R''$, $R_2 = NH\text{-}A\text{-}N(O)R'R''$ at position 5 and $R_3 = R_4 = OH$ at positions 7 and 10.

9. A compound according to claim 1, in which $R_1 = A\text{-}N(O)R'R''$ and $R_2 = R_3 = R_4 = H$, or $R_1 = A\text{-}N(O)R'R''$, $R_2 = NH\text{-}A\text{-}N(O)R'R''$ at position 5 and $R_3 = R_4 = H$, with $A\text{-}N(O)R'R''$ being $(CH_2)_n\text{-}N(O)(CH_3)_2$, $(CH_2)_n\text{-}N(O)(C_2H_5)_2$ or $(C_2)_n\text{-}N(O)(CH_2CH_2OH)_2$ and NH-A-N(O)R'R'' being $NH\text{-}(CH_2)_n\text{-}N(O)(CH_3)_2$, $NH\text{-}(CH_2)_n\text{-}N(O)(C_2H_5)_2$ or $NH\text{-}(CH_2)_n\text{-}N(O)(CH_2CH_2OH)_2$, wherein n is 2 or 3.

10. A compound according to claim 1, in which $R_1 = A\text{-}N(O)R'R''$, $R_2 = H$, $R_3 = OH$ at position 7 or 10 and $R_4 = H$ or $R_1 = NH\text{-}A\text{-}N(O)R'R''$, $R_2 = NH\text{-}A\text{-}N(O)R'R''$ at position 5 and $R_2 = OH$ at position 7 or 10, and $R_4 = H$, with $A\text{-}N(O)R'R''$ being $(CH_2)_n\text{-}N(O)(CH_3)_2$, $(CH_2)_n\text{-}N(O)(C_2H_5)_2$ or $(CH_2)_n\text{-}N(O)(CH_2CH_2OH)_2$ and NH-A-N(O)R'R'' being $NH\text{-}(CH_2)_n\text{-}N(O)(CH_3)_2$, $NH\text{-}(CH_2)_n\text{-}N(O)(C_2H_5)_2$ or $NH\text{-}(CH_2)_n\text{-}N(O)(CH_2CH_2OH)_2$, wherein n is 2 or 3.

11. A pharmaceutical composition comprising a compound of formula (I) as defined in claim 1 together with a physiologically acceptable diluent or carrier.

12. A method of treating a patient suffering from an anaerobic bacterial infection with a therapeutically effective amount of a compound of formula (I):

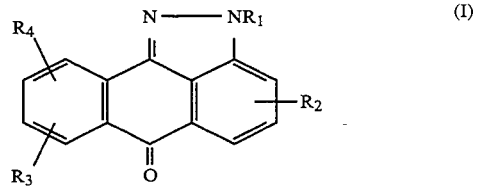

in which $R_1$ is $A\text{-}N(O)R'R''$ and $R_2$, $R_3$ and $R_4$ are each separately selected from hydrogen, X and NH-A-N(O)R'R'' wherein X is hydroxy, halogeno, amino, $C_{1-4}$ alkoxy or $C_{2-8}$ alkanoyloxy, A is a $C_{2-4}$ alkylene group with a chain length between N or NH and N(O)R'R'' of at least 2 carbon atoms and R' and R'' are each separately selected from $C_{1-4}$ alkyl groups and $C_{2-4}$ hyroxyalkyl and $C_{3-4}$ dihydroxyalkyl groups in which the carbon atom attached to the nitrogen atom does not carry a hydroxy group and no carbon atom is substituted by two hydroxy groups, or R' and R'' together are a $C_{2-6}$ alkylene group which with the nitrogen atom to which R' and R'' are attached forms a heterocyclic group having 3 to 7 atoms in the ring, the compound optionally being in the form of a physiologically acceptable salt.

* * * * *